(12) United States Patent
Janssen et al.

(10) Patent No.: US 6,465,259 B1
(45) Date of Patent: Oct. 15, 2002

(54) NON RADIOACTIVE RECEPTOR ASSAY SUITABLE FOR QUANTITATIVE AND QUALITATIVE ANALYSIS OF TRACE AMOUNTS OF RECEPTOR BINDING ANALYTE

(75) Inventors: Maria Johanna Janssen, Goirle; Kornelis Ensing, Roodeschool; Rokus Arie De Zeeuw, Appingedam, all of (NL)

(73) Assignee: Merska B.V., Groningen (NL)

( * ) Notice: Subject to any disclaimer, the term of this patent is extended or adjusted under 35 U.S.C. 154(b) by 0 days.

(21) Appl. No.: 09/297,027

(22) PCT Filed: Oct. 25, 1996

(86) PCT No.: PCT/NL96/00418

§ 371 (c)(1),
(2), (4) Date: May 6, 1999

(87) PCT Pub. No.: WO98/19166

PCT Pub. Date: May 7, 1998

(51) Int. Cl.$^7$ .................. G01N 33/531; G01N 33/533; G01N 33/542; G01N 33/16

(52) U.S. Cl. .................. 436/518; 436/43; 436/519; 436/800; 436/807; 436/809; 435/4; 435/5; 435/6; 435/7; 435/7.21; 435/7.22; 435/7.25; 435/7.92; 435/7.93; 435/7.94; 435/21; 435/69.4; 435/70.1; 435/71.2; 435/91.94; 435/172.1; 435/240.1; 435/320; 435/518; 435/538; 435/540; 435/962; 435/968; 530/300; 530/301; 530/324; 530/350; 530/351; 530/395; 530/397; 530/399; 530/402; 530/403

(58) Field of Search .................. 435/4–7, 7.21, 435/7.22, 7.25, 69.4, 21, 70.1, 71.2, 91.94, 172.1, 240.1, 320, 968, 7.92, 7.94, 7.93, 962, 518, 538, 540; 530/300, 301, 324, 350, 351, 395, 397–399, 402, 403; 436/43, 519, 518, 800, 807, 809

(56) References Cited

U.S. PATENT DOCUMENTS 3,901,654 A * 8/1975 Gross .................. 23/230 B

FOREIGN PATENT DOCUMENTS

| EP | 0264 797 | * 4/1988 | .......... G01N/33/531 |
| WO | WO 80/00750 | 4/1980 | .......... G01N/33/16 |
| WO | WO 93/03382 | 2/1993 | .......... G01N/33/94 |

OTHER PUBLICATIONS

McCabe et al., "Characterization of benzodiazepine receptors with fluorescent ligands". The FASEB Journal, vol. 4., Aug. 1990, pp. 2934–2940.*

Farde et al., "The substituted benzamides as ligands for visualization of dopamine receptor binding in the human brain by positron emission tomography.", Proceedings of the National Academy of Science, USA., vol. 82, pp. 3863–3867, Jun. 1985.*

Janssen et al., "Solubilized benzodiazepine receptors for use in receptor assays.", Journal of Pharmaceutical and Biomedical Analysis, vol. 14, pp. 989–996, Jun. 1996.*

Smisterova et al., "Methodological aspects of quantitative receptor assays.", Journal of Pharmaceutical & Biomedical Analysis, vol. 12, No. 6, pp. 723–745, 1994.*

Takeuchi et al., "Nonisotopic receptor assay for benzodiazepine drugs using time–resolved fluorometry.", Analytical Chemistry, vol. 67., pp. 2655–2658, 1995.*

Aranyi et al., "Determine rate constants of interaction of steroid receptors with non–labelled ligands.", Journal of Steroid Biochemistry, vol. 13, pp. 1167–1172, 1980.*

Batke et al., "Displacement analysis of binding inhomogeneities in crude extracts of receptors.", Journal of Biochemical and Biophysical Methods, vol. 12, pp. 203–212, 1986.*

Akera et al., "A simpler method for the determination of affinity and binding site concentration in receptor binding studies.", Biochimica et. Biophysica Acta, 470 (1977) pp. 412–423.*

Smisterova et al., "Evaluation of a purification procedure for the muscarinic receptor for the purpose of quantitative receptor assays of anticholinergics.", Preparative Biochemistry, 25(4), 197–221, (1995).*

T. Takeuchi et al., "Nonisotropic Receptor Assay for Benzodiazepine Drugs Using Time–Resolved Fluorometry", Analytical Chemistry, vol. 67, No. 15, Aug. 1, 1995, pp. 2655–2658, Washington, D.C.

Bosmann et al., "Diazepam receptor: specific binding of [3H]–diazepam and [3H]–flunitrazepam to rat brain subfractions.", FEBS Lett., 1978, vol. 87, No. 2, pp. 199–202. Abstract Only.*

* cited by examiner

Primary Examiner—Christopher L. Chin
Assistant Examiner—Lisa R Cook
(74) Attorney, Agent, or Firm—Young & Thompson

(57) ABSTRACT

A method for quantitatively and/or qualitatively assaying an analyte in a sample, wherein the analyte is a receptor binding compound, has low detection limits equivalent to those of radioreceptor assays. The method comprises the steps of a) contacting the sample with material comprising a receptor for the analyte in order for receptor-analyte binding to occur and b) further contacting the sample with a detectable ligand for the receptor in order for receptor-ligand binding to occur, followed by c) separating the resulting receptor bound and free fractions, d) subjecting the receptor bound fraction to dissociating conditions releasing the ligand from the receptor and e) assaying for the dissociated ligand in a manner known per se for the detection of the detectable ligand.

49 Claims, 5 Drawing Sheets

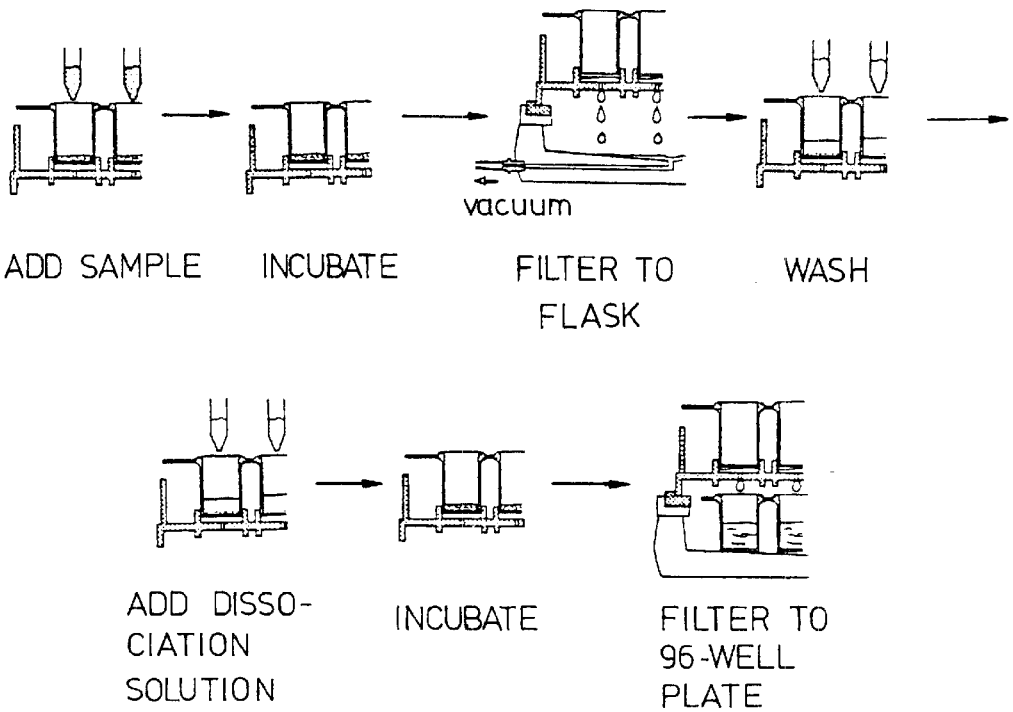
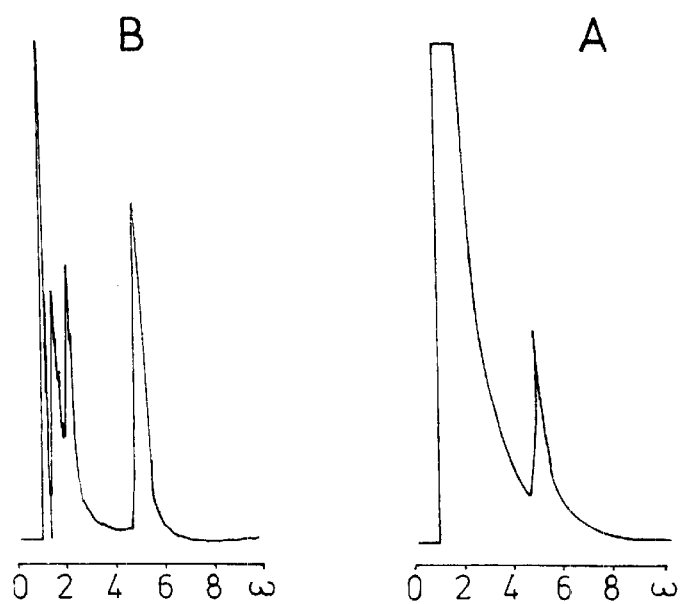

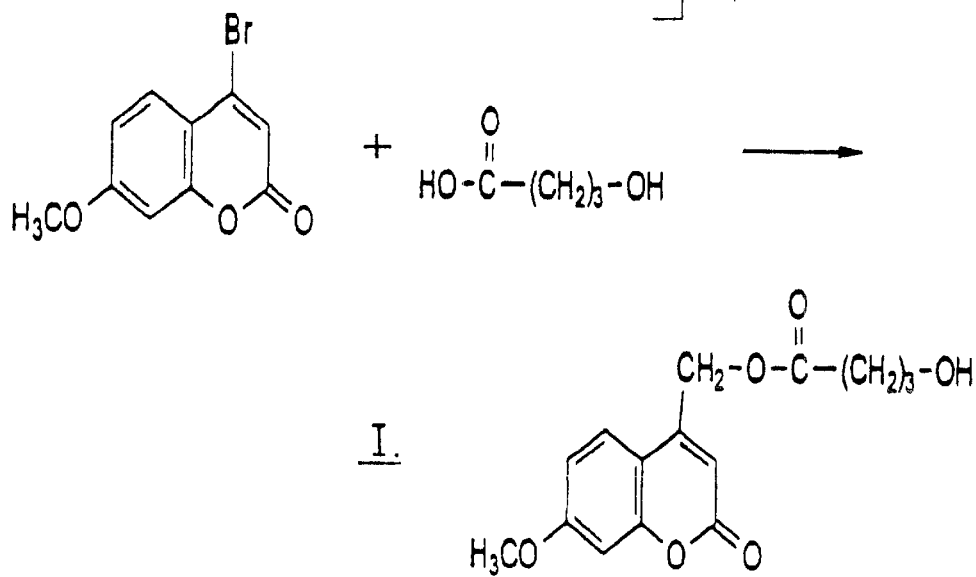
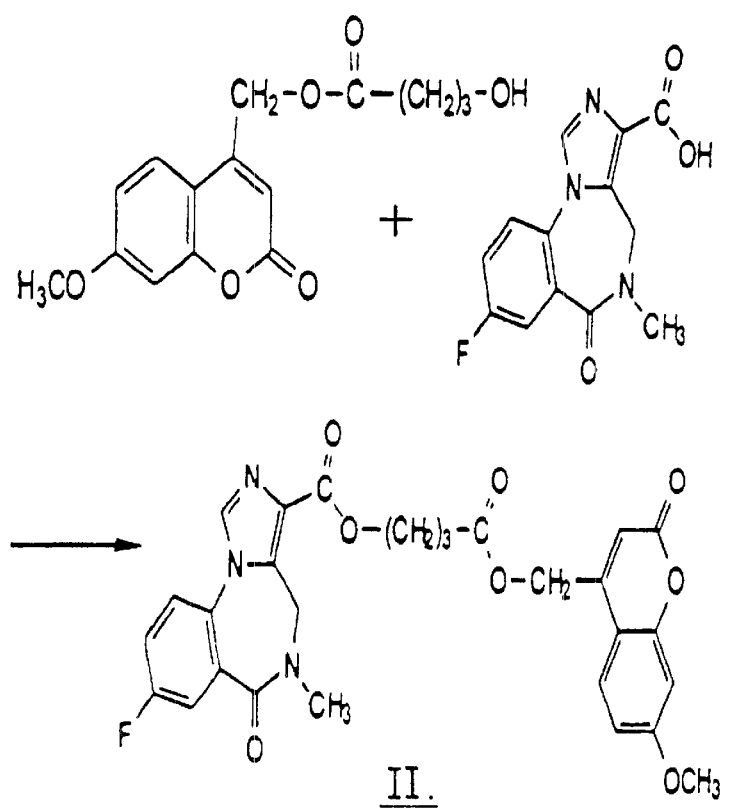
Fig-7

NON RADIOACTIVE RECEPTOR ASSAY SUITABLE FOR QUANTITATIVE AND QUALITATIVE ANALYSIS OF TRACE AMOUNTS OF RECEPTOR BINDING ANALYTE

BACKGROUND OF THE INVNETION

Receptor binding assays have been commonly employed for studying receptor ligand interactions in e.g. neurochemistry, neurobiology. psychopharmacology and related fields. Receptor assays are also used as an analytical method to measure drug levels in biological matrices. The principle of these methods is based on the competition of a labeled ligand and the analyte for binding to a certain receptor. Up till now, receptor assays have mostly been performed with radioactive ligands. Due to the low density of receptor binding sites in most tissue e.g. 10 to 100 pmol ligand bound per gram of tissue the ligand used must have high affinity and selectivity for the binding sites as well as high specific radioactivity in order to determine low levels of ligand. Radioactive ligands are commercially available that can be selectively measured at very low levels due to their high specific activity. Besides, since most of the radioisotopes are incorporated in the molecule, this type of labeling has no influence on the binding affinity of the ligand towards the receptor. Since the use of radioactivity has several well documented disadvantages such as limited shelf life, problematic handling and care required in the disposal thereof, non-radioactive ligands, such as fluorescent-labeled ligands, have been synthesized for different receptor types. To date however the results have not been such that reliable quantitative data for trace amounts of analytes can be obtained in a simple and satisfactory manner that they can offer an alternative for those types of analysis carried out with radioactive receptor assays (RRAs).

Examples of a non radioactive receptor assay are provided in general for a large number of receptors in WO93/03382 of Tyler McCabe. They describe how numerous attempts to characterize receptors using fluorescent ligands were carried out. The references cited on page 3 of the PCT application are hereby also incorporated by reference. The receptors mentioned are α-adrenergic β-adrenergic, opioid, adenosine, glucagon, steroid and dopamine receptors. They indicate there were problems with quantification and visualisation by direct fluorescence measurement due to autofluorescence and lack of specificity. They provide a group of fluorescent ligands suitable for determining ligand-receptor interactions intracellularly and extracellularly and to determine the specificity and affinity of uncharacterised compounds. They analyse intracellular versus extracellular events by selecting a fluorescent probe which emits different fluorescent intensities depending on the pH of the environment. They carry out their tests on 100% tissue. The receptors mentioned were opioid, potassium channel, glibenclamide and glycine. The assays actually illustrated are a fluorescein labelled ligand for the opioid receptor, nitrobenz-2-oxa-1,3-diazol-4-yl(=NBD) labelled ligands for the potassium channel and glibenclamide and glycine receptors. They indicate the fluorescent value is corrected for by subtracting the value of auto fluorescence. This means the assay they employ can never be sufficiently sensitive to obtain reliable quantification or detection of trace amounts of analytes.

One of the important receptors for pharmacologists and doctors is the benzodiazepine receptor. Benzodiazepines are extremely widely used drugs and have been primarily used for the treatment of anxiety and insomnia. It is accepted the pharmacological effects are medicated through specific receptors in the central nervous system. This receptor has been found to be extremely difficult to tackle for determining low concentrations of benzodiazepine receptor binding analytes. In vitro receptor radioligand interactions have been used to investigate the mechanism of the pharmacological effects and also to investigate new benzodiazepine drugs.

An alternative method has been the use of non radioactive immunoligand assays. These solve the problems associated with the use of radioactivity. The disadvantages thereof are however numerous. In immunoassays the binding molecule is an antibody that has been generated against the ligand to be determined. In order to generate antibodies the ligand must first be linked to a large carrier for example BSA. The position of the linkage of the BSA to the ligand restricts the selectivity of the antibody. The antibody is not selective for the linkage position. The sensitivity of immunoassays is not correlated to the pharmacological effectivity of the ligand. The affinity between ligand and antibody is based merely on chemical structure not an the chemical structure that determines the pharmacological effectivity. A ligand can have a high affinity for the antibody whet such Ligand is hardly pharmacologically effective and vice versa. For example the Merck label for the fluorescent polarisation immunoassay for benzodiazepines (Vitalab Eclair) hardly has any affinity for the benzodiazepine receptor (Ki=200 nM). With regard to metabolites nothing can be stated with regard to their pharmacological activity. In addition when multiple ligands need to be determined multiple antibodies are required for each separate ligand. In the receptor ligand assays a single ligand can suffice to assay for multiple analytes. The immunoligand technology is for example illustrated in EP-A-0.264.797 of Abbott.

Specifically for the benzodiazepine receptor for example fluorescent-labeled ligands have also been used as non radioactive labeled ligand for the characterization of the benzodiazepine receptor [g-i]. Such characterisation experiments however are not subject to the degree of sensitivity required for analyte detection and quantification at trace limits. The content of the cited articles will however be presented furtheron in order to create a more complete overview of the technology and the specific problems.

Further to the above more recent publications for the benzodiazepine receptor address use of fluorescent-labeled ligands as labeled ligand for a benzodiazepine receptor assay [b (1991),j (1993). c(1995)] as opposed to simple characterisation.

In the fluorescent benzodiazepine receptor assays developed by Takeuchi et al. [b,c], the free fractions of label were quantified after collection of these fractions by centrifugation. Since membrane-bound receptors exhibit background fluorescence [c] the problem of autofluorescent interference was expected to be reduced in these assays. However this was not the case. Additional measures were required and the sensitivity of these assays left a lot to be desired, Takeuchi and Rechnitz in [b] already in 1991 described quantifying the free fraction of the ligand. They used a HPLC-system in conjunction with AMCA-Ro7-1986 (AMCA-didesethylflurazepam) as ligand in their fluorescence receptor assay. The use of HPLC was required as a pretreatment to eliminate possible interference in the matrix. The supernatant after the bound/free separation by centrifugation was injected directly onto the HPLC column without further cleanup such as filtration. To obtain enough difference in the fluorescence signal between the maximal binding and the non-specific binding, they also had to use a high amount of receptor material, 50 mg/ml. Such a test is not practical for large scale commercial use due to the prohibitive cost of using such high amounts of receptor material. In addition the use of such high amounts of animal tissue is undesirable also from an ethical point of view.

Takeuchi et al. [j and c] later addressed the problem of autofluorescence in an alternative and preferred manner as disclosed in their articles of 1993 and 1995. Specifically they stated in the latter article "Because the commercially available benzodiazepine receptor preparations are only partially purified their supernatants exhibit strong background fluorescence and may interfere with the measurement of fluorophore labeled ligands". To solve this problem in the cited article they disclose developing a time-resolved fluorometric assay for benzodiazepines. They specifically state "radioligand receptor assays are frequently performed in laboratories as no feasible nonisotopic assays using drug receptors have been reported". They also provide the considerations for the development of nonisotopic receptor assays "the label may not significantly reduce the ligand affinity to the receptor land at the same time a highly sensitive measurement method for the labeled ligand must be available so sensitivity comparable to radioisotopic methods can be achieved." Their new process involved selection of a specific label with special fluorescent capabilities. They chose to use a europium chelate as label, since their supernatant exhibited strong background fluorescence which interfered with the measurement of the fluorophore-labeled ligands. The europium chelate provides a different type of fluorescence than the autofluorescence of the membrane material. The europium chelate provides a long lifetime fluorescence after excitation with pulsed light. This enables performance of time resolved fluorometry without interference front short term lifetime fluorescence of common fluorophores such as those present in the receptor matrix. They subsequently separated the bound and free fractions of their label, Eu-1021-S, by centrifugation and quantified the free fractions by the measurement of time-resolved fluorescence in the supernatant. The subject invention provides a suitable alternative and furthermore enables use of fluorescent labels that can also be determined at wavelengths in the area of the background fluorescence. The subject invention does not require time resolved fluorescence. The subject invention reaches higher sensitivity. To obtain enough difference in the fluorescence signal between the maximal binding and the non-specific binding, Takeuchi et al. also had to use a high amount of receptor material, 50 mg/ml. Such a test is no practical for large scale commercial use due to the prohibitive cost of using such high amounts of receptor material. In addition the use of such high amounts of animal tissue is undesirable also from an ethical point of view. As referred to above articles [g-i] dealt with characterisation of benzodiazepine receptors rather than quantification. Havunjian et al. [g] and McCabe et al. [h] do however describe how they quantified the bound fractions of their labelled ligands. However as disclosed above since membrane-bound receptors exhibit background fluorescence [c] and their measurements were executed in the presence of the receptor materials additional measures needed to be taken to overcome this problem. Specifically Havunjian used fluorescent-labeled benzodiazepine BD 623 (NBD-NH—$(CH_2)_3$-Ro15-3890, also known as NBD-desethylflumazenil) as a benzodiazepine ligand in assays monitoring fluorescence/dequenching. The bound fraction was determined. After determining the autofluorescence of the membrane preparation (autofluorescence) (region A, FIG. 2A of the cited article) BD 623 was added and fluorescence was monitored over time. Fluorescence was gradually quenched to a plateau (region C) when addition of excess flurazepam effected a dequenching of fluorescence that was monitored to equilibrium (region D). The use of SD 623 as a prototype for the development of other fluorescent ligands to study ligand receptor interactions was postulated. In practice the assays were found to be insufficiently sensitive to provide an assay capable of detecting low amounts of analyte. They required high amounts of ligand, in the example provided the amount of ligand works out at approximately 10*Kd. They also required high amounts of receptor material. Havunjian discloses "The use of receptor densities 20–80 fold higher in fluorescence compared to radioreceptor assays . . . ". In this method, it is remarkable that they can detect the amount of quenching of NBD-NH—$(CH_2)_3$-Ro15-3890, specially regarding the low quantum yield of the fluorophore NBD, which is 0.02 in Tris-citrate buffer (pH 7.4; 50 mM) [g]. They did not present a feasible alternative to radio receptor ligand assays.

The Tyler McCabe article [h] (of a later date than the previously cited PCT application of this author) addresses the problems associated with radioassays and postulates the application of fluorescence as an alternative. Two benzodiazepine ligands labeled with fluorophores are presented fluorescein-NH—$(CH_2)_3$-Ro15-3890 (BD 621) and (BD 607) the direct coupling product of Ro-7-1986 with carboxyfluorescein-N-hydroxysuccinimide ester in DMF. BD 621 is a fluorescein desethylflumazonil derivative and BD 607 is a fluorescein didesethylflurazepam derivative. McCabe et al. measured the bound fractions of their fluorescent-labeled benzodiazepine. After separation of the bound and unbound fractions by centrifugation, they resuspended the pellet in buffer and measured the fluorescence intensity of the suspension. The fluorescently labelled ligand was still bound to the receptor during the measurement. No indication of detection limit is provided. High amounts of ligand and high amounts of receptor for a sensitive assay following the teaching of this document would be envisaged. It is remarkable their fluorescent-labeled benzodiazepine could in fact even be detected in the presence of the receptor material. However, fluorophore fluorescein has relatively high excitation and emission wavelengths ($\lambda_{ex}$= 499 nm and $\lambda_{em}$=521 nm) in comparison to other fluorophores, such as a coumarin derivate. The autofluorescence of the receptor material is less at higher wavelengths, which could explain the matter. Nevertheless the interference will still be enormous. They themselves even found that the fluorescence intensity of fluorescein-NH—$(CH_2)_3$-Ro15-3890 was stronger when measured in tissue suspension than when measured in buffer only and that this increased intensity was not due to the background fluorescence of the tissue suspension. The Kd values of the fluorophores illustrated are 63 and 74 which render them incapable of sufficient sensitivity for application in detecting and quantifying trace analytes. In practice tho assays were insufficiently sensitive to provide an assay capable of detecting low amounts of analyte and required high amounts or receptor material.

It is an objective of the subject invention to provide a highly sensitive receptor-ligand assay that does not require dealing with radioactivity but provides a test with at least the sensitivity and specificity of a radioactive receptor assay. Such an assay must be simple to execute and economically feasible enabling routine laboratory application.

SUMMARY OF THE INVENTION

The subject invention provides a highly sensitive receptor-ligand assay that does not require dealing with radioactivity but provides a test with at least the sensitivity and specificity of a radioactive receptor assay. Such an assay is simple to execute and economically feasible enabling routine laboratory application. Also a group of ligands specifically directed at benzodiazepine receptors suitable for use in an essay according to the invention is provided.

Figure 1:
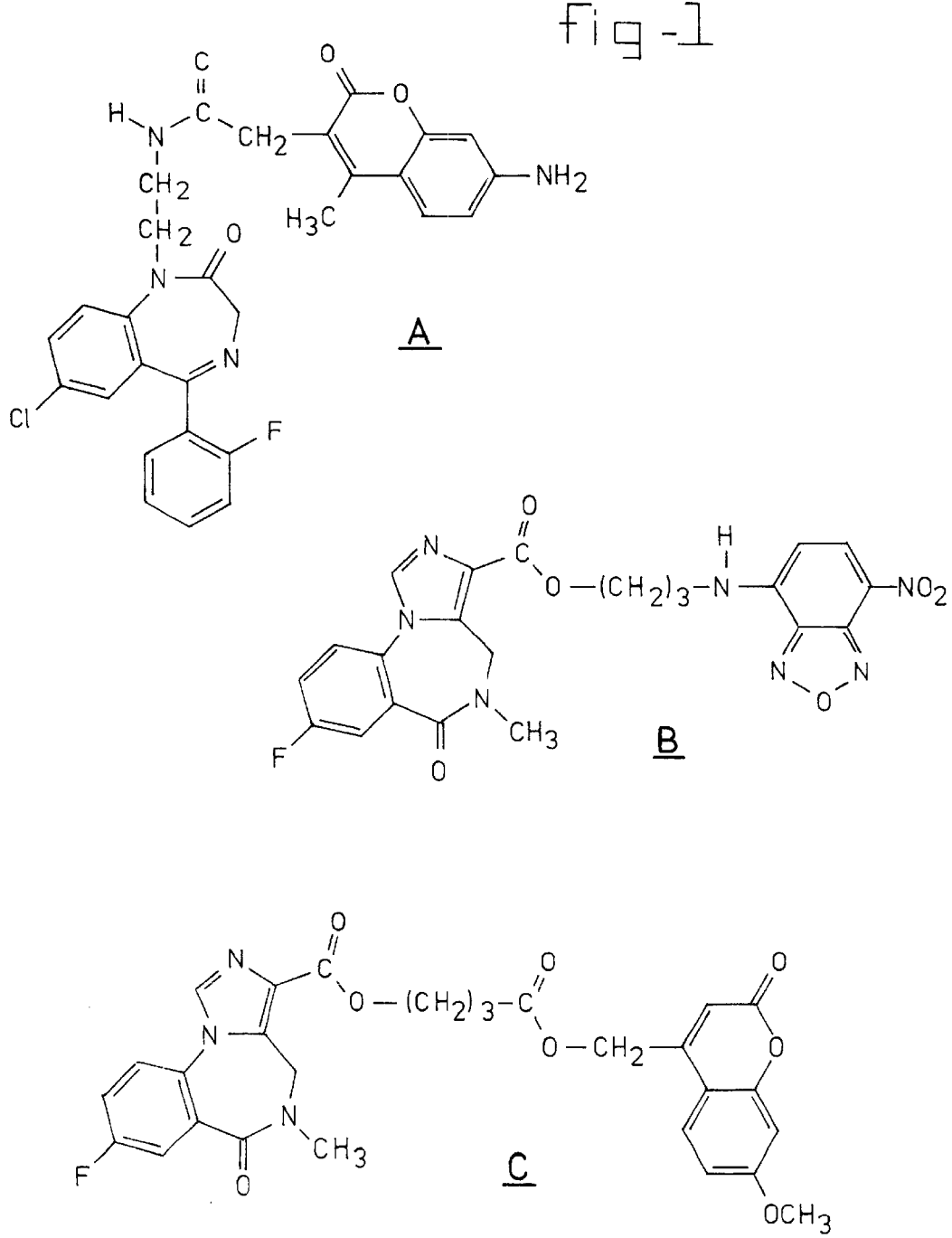
FIG. 1

Structure of 3 compounds suitable for fluorescent assay according to the invention. The compounds are a) AMCA-Ro7-1986
   $K_1$=8.6 nM [b]
b) Mmc—O—CO—$(CH_2)_3$-$Ro_{15}$-3890
   $K_1$=6.5 nM
c) NBD—NH—$(CH_2)_3$-Ro15-3890
   $K_1$=5.7 nM

FIG. 2

Principle of the fluorescent receptor assay for benzodiazepines.

FIG. 3

Chromatograms of 10 nM FLB, (A) in Tris-HCl buffer (pH 7.4; 50 mM), containing 10 $\mu$M flumazenil and (B) in acetate buffer (pH 4; 100 mM).

FIG. 4

Saturation curve of FLB for the benzodiazepine receptor. ■ represents the total binding, ● the specific binding and ▼ the non-specific binding.

FIG. 5

Calibration curves of different benzodiazepines: diazepam (●), lorazepam (▼) and flumazenil (■).

FIG. 6

Comparison of calibration curves of lorazepam with different types of labeled ligands: ● represents an assay performed with [$^3$H]flunitrazepam (2.2 nM final concentration) and ▼ represents an assay performed with FLB (7.3 nM final concentration).

FIG. 7

Preparation method for FLB

Contents of the references mentioned in the description are hereby incorporated by reference.

DESCRIPTION OF THE PREFERRED EMBODIMENTS

The subject invention provides a method for quantitatively and/or qualitatively assaying an analyte in a sample, said analyte being a receptor binding compound, said method having low detection limits equivalent to those of a radioreceptor assay for said receptor said method comprising the steps of a) contacting the sample with material comprising a receptor for said analyte in order for receptor-analyte binding to occur and
b) further contacting the sample with a detectable ligand for the receptor in order for receptor-ligand binding to occur, followed by
c) separating the resulting receptor bound and free fractions,
d) subjecting the receptor bound fraction to dissociating conditions releasing the ligand from the receptor and
e) assaying for the dissociated ligand in a manner known per se for the detection of the detectable ligand.
   said receptor being present in a concentration between 0.5–5 nM.
   said detectable ligand being at least 90% pure,
   said detectable ligand being non radioactively detectable,
   said detectable ligand being added in an amount corresponding to the amount required for occupation by the ligand of 10–75% of the receptor material present in the assay in absence of analyte at a receptor concentration below the $K_d$ of the ligand and receptor under conditions otherwise corresponding to those of the assay.
   said dissociating conditions and said detectable ligand being such that at least 90% bound ligand is released in such a form that less than 10% of the resulting detectable product reassociates with the receptor,
   said dissociating conditions and said detectable ligand being selected such that the resulting dissociated product is quantitatively and/or qualitatively detectable. The ligand and dissociating conditions can be selected such that the ligand does not degradate and thus forms the detectable product or such that degradation of the ligand occurs completely and uniformly yielding a detectable product.

Preferably the affinity of the dissociated ligand from the receptor for the receptor will be nihil or as close to nihil as possible. The detectable product can be the ligand after dissociation as such or be attached to the detectable label. The detectable product can also be the degradation product comprising label no longer attached to the ligand or attached to a degraded form of ligand. The steps a) and b) can be carried out concomitantly. In a preferred embodiment step a) is carried out prior to step b) in order to enable establishment of controlled non-equilibrium, providing greater sensitivity.

In particular the method according to the invention is directed at carrying out assays wherein the analyte is to be detected at a level below 1 $\mu$M. The assay can also even be carried out successfully on analyte levels below 100 nM. most preferably below 50 nM. Preferably the method according to the invention is carried out to ascertain as low analyte levels as possible. With a view to developing potent drugs and analysis of their activity levels analyte concentrations as low as 1 picomolar but also as low as 100 femtomolar are of interest.

In a method according to the invention a suitable embodiment comprises adding ligand in an amount equivalent to an amount within the range 0.1–2.0*$K_d$ nM of the receptor and ligand. Preferably the ligand is added in an amount between 0.5–1.5*$K_d$ nM. Quite suitably an amount approximately 1 Kd nM is applied. For a large number of ligands Kd values are already available from handbooks. A person skilled in the art can also ascertain in a manner known per se what the Kd value is for a particular ligand and receptor. In general a detectable ligand with a $K_d$ value for the detectable ligand and receptor below 10 nM is an excellent candidate for use in the assay according to the invention. Such a Kd ensures the required sensitivity for detecting and quantifying trace analytes.

In the method according to the invention step c) can be carried out in a number of manners which will be apparent to a person skilled in the art. It will depend on the nature of the receptor material whether additional pretreatment steps prior to separation ale required. The simplest way of carrying out step c) comprises separating the bound fraction on the basis of size difference from the free fraction. In the case of membrane bound receptor material the separation can e.g. occur simply via filtration. In an embodiment of the invention the free fraction is separated in step c) from the bound fraction by filtration. Alternatively centrifugation could be applied. In an embodiment whereby the bound fraction is retained bit the filter and the free fraction passes through the filter the amount of receptor material must be such that the amount of receptor is less than the amount of receptor material that will clog the filter. By way of example the amount of receptor is less than 1–4 mg/ml lyophilised receptor material when the assay volume equals 0,25 ml i.e. 4–16 mg/ml receptor material/ml assay volume when using a filtertype as present in MultiScreen-FB™ filtration plates of Millipore™ or of equivalent type. Whatman GFB filter material is suitable. Alternatively the amount of receptor material when the separation step uses a filter is lower than the amount of receptor that will clog the filter when the amount of receptor is less than 1–4 mg/ml lyophilised receptor material per 0,2 cm$^2$ of filter area when using filtertype as present in MultiScreen-FS filtration plates of Millipore or of equivalent type as mentioned above. A combination of the two requirements is also possible.

A more specific embodiment of the invention is a method as defined in general terms above comprising the steps of a) contacting the sample with material comprising a receptor for the analyte in order for receptor-analyte binding to occur and b) further contacting the sample with a ligand for the receptor in order for receptor-ligand binding to occur in a container comprising a filter, said filter being of such a nature to ensure the receptor material cannot pass the filter whereas the smaller particles in particular the non bound ligand and analyte can, c) separating the resulting receptor bound and free fractions by filtering the resulting mixture and rinsing the filter, d) subjecting the receptor bound fraction as present in and on the filter to dissociating conditions releasing the ligand from the receptor and passing the resulting solution through the filter into another vessel in order for detection or the dissociated detectable product to occur in a manner known per se for the detection of such detestable product.

The method according to the invention can be carried out using membrane bound receptor material as illustrated for the benzodiazepine receptor. Alternatively however soluble or solubilised receptor material can be applied. Some modification of the method when using the different types of receptor is required due to the different nature of the receptor materials, but the basic methodology is the same as will be clear to a person skilled in the art who is aware of the differences in soluble receptor material, solubilised receptor material and bound receptor material. In a method according to the invention wherein the receptor material is soluble or solubilised receptor material and said material has been subjected to treatment enabling separation via filtration in step c) as disclosed above for the method according to the invention in general treatment ensuring the receptor bound fraction cannot pass the filter upon filtration in a manner known per se is additiorally required. An example of such treatment comprises precipitation with protamines prior to the actual filtration step. Alternative measures to achieve the separation step will be apparent to a person skilled in the art of free/bound fraction separation.

It is commonly known that ligand receptor binding can be very sensitive to size and location of the detectable label on the ligand. Linkage of label to ligand can negatively influence the binding affinity for the receptor. The most favorable location for such linkage and also places impossible for such linkage have been assayed for numerous ligands. Naturally for application in the subject method the ligands with label only in such favorable location can be considered. In addition to the general location of label the degree to which affinity is affected also depends on the nature of the fluorophore. A small fluorophore may not negatively influence the binding to the degree a large fluorophore may. In the case of a detectable ligand being a ligand provided with an additional detectable label it is sometimes preferable with a view to maintaining the correct degree of specificity and sensitivity to provide the ligand with a detectable label that is attached via a spacer. In general when using a spacer linking label and ligand the spacer comprises a carbon chain of between 2–10. preferably 2–6 carbon atoms. The general requirements for the detectable ligand are summarised in the general definition of the method according to the invention. Suitable examples are provided. The suitable ligands can be determined by the person skilled in the art using details readily available concerning affinities and receptor binding structures. We illustrate this for the fluorescent labelled ligands of the benzodiazepine receptor. A number of suitable ligands already exist and naturally it is possible to prepare numerous ligands on the basis of the information presented in the subject application which can be suitably applied in the subject invention. Preferred labelled ligands will be those readily synthesized. We provide an example of a fluorescent compound that can be readily produced. We also refer to article [h]. which illustrates the preparation of labelled ligands. Such methods can be easily adapted to suit the specific details of the labelled ligand to be made and illustrate the principle of the simple chemistry involved. In our method a spacer was, linked to the fluorophore and subsequently to he ligand. The spacer used comprised a terminal carboxy group. McCabe used a terminal amino group for their spacer, which spacer was linked to the ligand following a slight adaptation of the ligand to a hydrolysed derivative. The fluorophore was subsequently linked to the ligand-spacer construct. The McCabe method requires protection and deprotection of the spacer reactive group used for linking the fluorophore. Such synthesis requires more steps and thus is not a preferred method of production of labelled ligand.

With regard to the dissociating conditions used in the assay this can comprise rinsing in conditions other than physiological conditions and under conditions which ensure the detectable product ie. ligand or detectable label of the ligand remain stable and functional. This implies the use of conditions which in addition to the fact they are non-physiological are not too agressive. The term "other than physiological conditions" preferably implies excluding use of conditions with a pH between 6–8. The term physiological conditions is an art recognised term and indicates the conditions that prevail in the body in vivo. The dissociation conditions according to the assay can comprise a weak buffer i.e. with a pH between 3.5 and 4.5, preferably between 3.75 and 4.25. An acetate buffer is a suitable example of a buffer for dissociating under not too agressive circumstances.

In order to reduce background fluorescence to a minimum the dissociating conditions mentioned above and said receptor material mentioned above should be such that no other compounds are released in an amount that can interfere with the detection of the released detectable product. In the case of the benzodiazepine receptor binding ligands for example a flumazenil derivative provides an excellent embodiment of this kind. It exhibits close to no affinity after dissociation as is clear from the example provided elsewhere.

In a preferred embodiment of the invention the fraction resulting from the dissociation step comprising the dissociated free detectable product is assayed using a HPLC chromatograph linked to a detector of the type required for detecting the detectable product. This reduces the risk of interfering fluorescence due to contaminating autofluorescent receptor particles or other fluorescent contaminants. Alternatively the fraction resulting from the dissociation step comprising the dissociated free detectable product is assayed using GLC linked to a detector of the type required for detecting the detectable produce. Other methods of separation can also be used and will be apparent to a person skilled in the art between the dissociation step and detection step.

In a method according to the invention the receptor material is preferably washed at least three times prior to contacting the sample with analyte in order to reduce the risk of interfering contamination. Subsequently the detectable product can be determined via any number of non-isotopic detection methods depending on the type of ligand and/or label used. Suitable examples of detection methods are FID=(flame ionisation detection), ECD=(electron capture detection), NPD=(nitrogen phosphor detection) and mass spectrometry. Other methods also comprise electrochemical detection, fluorescence, chemoluminescence and luminescence. All these technologies are well known and details concerning their application are well publicised and within reach of a person skilled in the art without requiring an undue burden. Numerous hand books and general text books describe such methods and apparatus for carrying out such methods arc commercially available.

In particular the field wherein the detectable product is a ligand as such that is detectable with fluorescence technology or is a ligand provided with a label that is capable of being detected by fluorescence technology is a suitable embodiment. Non-time resolved fluorometry now becomes a feasible option for detections as the problem due to autofluorescence of receptor material is overcome. A large number of fluorescent labels are available. In particular we have found a number of fluorescent labels falling within the group defined above. Such labelled ligands and/or the detectable products after the dissociation step must have the required minimal affinity as defined elsewhere for the method. The labelled ligand must be stable. The labelled ligand or detectable product obtained after being subjected to the dissociation conditions of the assay must have reduced affinity for the receptor material as also defined elsewhere for the method. Preferably the labelled ligand or detectable product obtained will have no affinity after the dissociation. A preferred group of labelled ligand or detectable product obtained has reduced affinity and preferably no affinity after hydrolysis. The affinity reduction required is also described elsewhere in this description. The fluorescent groups AMCA, NBD and a coumarin derivative have provided excellent characteristics. The coumarin derivative is more preferred die to the higher fluorescent signal it provides in aqueous solution than the NBD. Specifically the resulting fluorescent labelled ligands exhibited the required affinity values when the fluorophores were linked to the ligands didesethylflurazepam and desethylflumazenil respectively. Didesethylflurazepam and desethylflumazenil are suitable benzodiazepine ligands with high specificity and affinity. Three suitable compounds of this nature or benzodiazepine receptor assays according to the invention have Ki of 8.6 nM, 5.7 nM and 6.5 nM respectively and comprise a spacer. The structural formulas are provided in the FIG. 1. A particularly suitable compound for benzodiazepine receptor binding is the fluorescent ligand FLB (Mmc-O—CO—(CH$_2$)$_3$-Ro15-3890) illustrated in the figure. This compound as such is in fact also a novel compound and due to its extreme suitability in an assay according to the invention is also considered to be a part of the invention, NBD is a relatively small apolar group and linkage through a spacer prevents sterical hindrance. Similarly sized groups should also be useful. The development of suitable ligands using known data and computer modelling around the three compounds we have illustrated to be suitable should further provide alternative embodiments. With regard to the requirements for the benzodiazepine receptor binding we refer to the articles [a] and [e]. Such articles can provide insights into alternative benzodiazepine receptor high affinity ligands. Such novel compounds and use of novel compounds as described with the defined characteristics in a process requiring binding to a benzodiazepine receptor in a manner analogous for other receptor ligand binding requiring processes is also considered to fall within the scope of protection of the subject invention.

The flumazenil derived compounds e.g. have extremely low affinity for the benzodiazepine receptor after hydrolysis and for this reason form a preferred group of ligands for benzodiazepine receptors.

A particularly suitable compound for oestrogen receptor binding is the detectable ligand coumestrol. Coumestrol is an example of a ligand that does not need labelling because it possesses fluorescent characteristics per se.

The selection of label will depend i.a. on the receptor material to be assayed as well as the sample conditions. Fluorescence characteristics are known to vary with conditions. One type of label will be suitable in an aqueous medium whereas another will be suitable in a non aqueous medium. In particular in the field of drugs and testing of samples it will be preferred to apply detectable ligands providing optimal signal in an aqueous system such as an aqueous solution. Bodily fluids will generally form the sample to be tested in such cases, so the detectable ligand ray be selected accordingly. In a suitable embodiment according to the invention the detectable product provides a detectable signal in the test medium sufficient for reliable quantification i.e. exhibiting a deviation of less than 10% from the real value. A preferred embodiment of the invention comprises use of a ligand that provides such a detectable signal in aqueous medium to such a reliable degree. Suitably a fluorescent signal in aqueous medium with at least the strength of 0.2*the signal of 1M quinine standard in 1M H$_2$SO$_4$ can be applied to achieve this.

The method according to the invention can be carried out with receptor material that is membrane bound receptor material. In an alternative embodiment membrane receptors known in the art as soluble or solubilised receptors can also be used. Examples of membrane receptors are adenosine, adrenergic, dopamine, histamine, muscarinic (or acetylcholinergic), nicotinic, opiate, serotin, benzodiazepine, GABA., glycine, calcium channel, sodium channel, chemotactic peptide, EGF (epidermal growth factor), glucocorticoid, cannabinoid, cholecystokinin, cytokines, leukotriene and neurokinin receptors. These membrane receptors can be extracted from the embedding membrane by a.o. detergents yielding solubilized receptors. Examples of soluble receptors are steroid hormone receptors, androgen, progesteron and estrogen receptors. Oestrgen receptor, benzodiazepine and cytokine receptor assays using the assay as defined according to the invention are of particular interest.

The receptor material used in the assay according to the invention can be derived from receptor containing tissues. The receptor material can be native receptor material obtained in vivo from an animal or microorganism. The material can be obtained from preparations derived from animal bodies as such. Brain material e.g. can comprise the desired receptors. The receptor material can also be obtained from tissue culture or cell culture. In principle at the moment there are numerous commercial sources of receptor material that can be used. It is preferable to use as pure a material as possible. However depending on the application desired the degree of purity required will vary. Another parameter that will exert an influence upon the selected source of receptor material will be the price of the receptor material. Receptor material that has been pretreated in the manner generally required for body samples comprising receptor material resulting in a P2 pellet is sufficiently pure for carrying out the assay according to the invention. As stated more purified receptor material can also naturally be used. When carrying out the assay in any of the embodiments described above an amount of receptor material can be used that is equivalent to that present in P2 pellet derived from receptor containing tissue, said P2 pellet having a concentration equal to 0.5–5 pmol/mg protein.

EXAMPLE

Fluorescent Receptor Assay for Benzodiazepines

In this embodiment of our fluorescent receptor assay, the bound and unbound fractions of FLB were separated by filtration Since FIB could not be measured in the presence of receptor material, due to its autofluorescence, we dissociated FLB before quantifying the bound FLB. This was achieved by incubating the FLB bound to the receptors with a weak acetate buffer (pH 4) after the first filtration. The second filtrates then contain the bound FLB. For the quantification of the bound fractions of FLB, we used a RP-HPLC system with a fluorescence detector. This was done since the filtrates also contained some impurities of the receptor material and fluorescence detectors for chromatographic purposes appeared to be more sensitive than conventional static fluorescence detectors.

We conclude that Mmc-O—CO—$(CH_2)_3$-Ro15-3890 (FLB) is an excellent choice of fluorescent-labeled benzodiazepine for use as labeled ligand in the fluorescent receptor assay for benzodiazepines. In this Example, we describe the use of FLB as fluorescent-labeled ligand for the benzodiazepine receptor assay. The binding of FLB towards the benzodiazepine receptor was established by performing saturation experiments. Further, calibration curves or three benzodiazepines, diazepam, lorazepam and flumazenil were determined with FLB as label. The calibration curve of lorazepam was also compared with a calibration curve obtained with the radioactive-labeled ligand [$^3$H] flunitrazepam. The results show that FLB can replace the radioactive-labeled ligand [$^3$H]flunitrazepam successfully.

2 Materials and Methods
2.1 Chemicals

[N-methyl-$^3$H]flunitrazepam (82.0 Ci/mmol) was obtained from DuPont NEN (Wilmington, Del., USA). Lorazepam was a gift from Wyeth Laboratoria B. V. (Hoofddorp, The Netherlands). Flumazenil and diazepam were a gift from Roche Nederland B. V. (Mijdrecht, The Netherlands). The synthesis and purification of the fluorescent labeled benzodiazepine FLB, structure see FIG. 1. is described elsewhere in the description. Methanol and acetonitrile were of hplc-grade and obtained from Lab-Scan (Dublin, Ireland). All other chemicals were of analytical grade and were purchased from Merck (Darmstadt, Germany).

The MultiScreen-FB filtration plates were kindly donated by Millipore (Etten-Leur, The Netherlands). Rialuma, used as scintillation cocktail, was obtained from Lumac (Olen, Belgium).

Demineralized water was further purified by an Elgastat Maxima instrument (Elga, High Wycombe, UK) before use in the buffers.

Synthesis of FLB was Carried out as Follows 265 mg 4-hydroxybutyric acid (sodium salt) and 1.95 g potassium carbonate were suspended in 200 ml acetonitrile. To this suspension, 37.5 mg 18-crown-6 and 375 mg 4-bromomethyl-7-methoxycoumarin were added and the whole was incubated et 65° C. for 1 hour. After the derivatization, the sediment formed was removed bed filtration and the acetonitrile was evaporated under vacuum. The residue was dissolved in 50 ml chloroform. The chloroform was washed six times with 20 ml water, dried with anhydrous sodium sulphate and after evaporation under vacuum, 1-(4-hydroxybutyryl)-oxymethyl-7-methoxycoumarirn was collected. For the labelling of desethylflumazenil, 87.7 mg desethylflumazenil (Ro15-3890) was dissolved in 5 ml dry dichloromethane and 200 μl dry triethylamine were added. The reaction mixture was cooled on ice and 40 mg methanesulfonylchloride was added. After incubation at room temperature for 1 hour, the mixture was cooled on ice again, 100 mg 1-(4-hydroxybutyryl)-oxymethyl-7-methoxy-coumarin was added and the reaction was continued at room temperature during the night. After the derivatization, the dichloromethane was evaporated and the residue was resuspended in 10 ml dry benzene. The precipitate was removed by filtration and the benzene fraction was evaporated under vacuum. This residue was dissolved in 50 ml dichloromethane. The dichloromethane was washed three times with 20 ml water, dried with anhydrous sodium sulphate and evaporated. The residue was dissolved in othylacetate and recrystallized from hexane. The Mmc-O—CO—$(CH_2)_3$-Ro15-3890 was further purified with RP-HPLC.

2.2 HPLC-system

The chromatographic system consisted of a SP 8800 HPLC-pump (Spectra physics, San Jose, Calif. USA). an autosampler model 460 fitted with a 120 μl loop (Kontron Instruments, Basle, Switzerland). a F-180 fluorescence detector, equipped with a 40 μl cuvette and 30 nm slit. (Merck-Hitachi. Darmstadt, Germany) and a 2 bar backpressure regulator (Merck, Darmstadt, Germany). Peak heights were recorded with a BD 8 recorder (Kipp & Zonen, Kronberg,).

The separation was performed using a 125*4 mm i.d. column packed with 5 μm LiChrospher® 100 RP-18 (Merck, Darmstadt, Germany). The mobile phase consisted of 40% denineralized water, 40% methanol and 20% acetonitrile. The flow rate was 1.0 ml/min. Mmc-CO—$(CH_2)$-Ro15-3890 was detected at $\lambda_{ex}$ 318 nm and $\lambda_{em}$ 400 nm.

2.3 Preparation of membrane-bound reeeptors

Calf brains, obtained from the slaughterhouse and stored at −80° C. after discarding the cerebellum, were homogenized in 6 volunmes (w/v) of ice-cold 0.32 M sucrose in a Potter-Elvehjem homogenizer (RW 20 DZW. Janke & Kunkel K G, Staufen i. Breisgau, Germany) fitted with a teflon pestle and centrifuged for 10 min at 1,000 ×g in a Beckman L8–55 Ulcracentrifuge (Beckman Instruments, Mijdrecht, The Netherlands). The supernatant was centrifuged for 60 min at 100,000×g. The resulting pellet ($P_2$) was resuspended in sodium phosphate buffer (pH 7.4; 50 mM) and centrifuged for 30 min at 100,000×g. This washing step was repeated four times. All operations were performed at 4° C. The washed $P_2$-pellet was resuspended in 5 volumes (w/v) phosphate buffer, frozen with liquid nitrogen and lyophilized (Hetosicc CD 52-1, Heto, Birkerød, Denmark) . rhe lyophilized $P_2$-pellet was stored at −20° C. For the receptor binding assays, the lyophilized $P_2$-pellet was resuspended in Tris-HCl buffer (pH 7.4; 50 mM) with the glass-teflon Potter homogenizer (3.5 mg/inl).

Protein amount was determined according to the method described in earlier experiments [d] with bovine serum albumin as standard.

2.4 Radioligand binding assay

The filters of a MultiScreen-FB filtration plate were pre-wetted by pipetting 200 µl ice-cold Tris-HCl buffer (pH 7.4; 50 mm) into each well. After waiting for at least 5 sec, vacuum was applied by the MultiScreen vacuum manifold (Millipore, Etten-leur, The Netherlands). For the binding assay, 25 µl Tris-HCl buffer, containing lorazepani (30 pM–100 nM final concentration) and 25 µl [$^3$H] flunitrazepam solution (2.2 nM final conzentration) in Tris-HCl buffer were pipetted in duiplicate into the wells of the filtration plate. To this ulixture 200 µl receptor suspension. were added and the plate was shaken for 1 min. After the incubation for 45 min at 4° C., vacuum was applied (400 mbar) and the filters were rinsed once with 200 µl ice-cold buffer. To dissociate the bound [$^3$H]flunitrazepam, 200 µl acetate buffer (pH 4; 100 mM) were pipetted in each well and incubated for 20 min at room temperature. The dissociation solutions were collected in a microtiterplate by filtration. Hundred µl of the filtrates were transferred into 6 ml polyethylene counting vials and dispersed in 3.5 ml Rialuma. After shaking the vials, the radioactivity was counted for 5 min in a Tri-Carb 4000 Packard scintillation counter (Canberra Packard, Groningen, The Netherlands). The binding experiments were performed in duplicate.

2.5 Fluoreacent binding assay

For the saturation experiments, 25 µl FLB solution (0.5–50 nM final concentration) in Tris-HCl buffer (pH 7.4; 50 mM) were pipetted in duplicate in the wells of the filtration plate after pre-wetting the filters. For the detercination of total binding, 25 µl Tris-HCl buffer were added and for the determination of non-specific binding, 25 µl Tris-HCl buffer containing 100 µM flumazenil. To this mixture, 200 µl of the receptor suspension (225 µg protein per assay) were added and the plate was shaken for 1 min. After incubation for 45 min at 4° C., vacuum was applied (400 mbar) and the filters were rinsed once with 200 µl ice-cold buffer. To dissociate the bound FLB, 200 µl acetate buffer (pH 4; 100 mM) were pipetted in each well and incubated for 20 min at room temperature. The dissociation solutions were collected in a microtiterplate by filtration and transferred in 300 µglass microvials (Phase Sep, Waddinxveen, The Netherlands). Hundred µl of the filtrates were analyzed with the above described HPLC-method.

To quantify the amount of FLB in the filtrates, a calibration curve was made by diluting five different solutions of FLB in Tris-HCl buffer with a 100-fold with acetate buffer to get the concentrations of 0.3; 0.5, 1.5; 3.0 and 5.0 nM. The calibration samples were analyzed in duplicate. For the calibration curves, the procedure was identical 1.0 the saturation experiments. Here 25 µl FLB solution (73 nM final concentration) in Tris-HCl buffer was mixed with 25 µl of a solution of diazepam (1 nM–1 µM final concentration), of lorazepani (0.3 nM–300 nM final concentration) or of flumazenil (30 pM–30 nM final concentration).

3 Results and Discussion 3.1 Principle of the Fluorescent Receptor Assay

The principle of the fluorescent receptor arsay in this embodiment is shown in FIG. 2. After separation of the bound and unbound fractions of FLB by filtration, the bound FLB was dissociated from the benzodiazepine receptor This was done to obtain the FLB in a solution, free from receptors and filter materials, so the amount of FLB could be determined easily by measuring the fluorescent signal. Instead or measuring the bound fraction of FLB, it was also possible to determine the free fraction of FLB. In this case, the filtrates had to be collected during the first filtration step. Since only 26% of the added FLB at an assay concentration of 7.3 nM was bound to the receptors (total binding), the bound fractions were quantified for a more accurate measurement.

3.2 The HPLC-system

The amount of bound FLB was quantified by HPLC. The HPLC-systein was used as the fluorescence detectors for chroliiatographic purposes are more sensitive than static fluorescence spectrometers for cuvettes Besides, after the dissociation, the dissociation solutions also contain some impurities, which are released by the receptor material, the this reason, during the preparation of the membrane-bound receptor material, the $P_2$-pellet was washed 5 times instead of 2 times, according to our standard procedure [d]. Using a HPLC-system for quantification of FLB, the FLB can be separated from these impurities.

The mobile phase composition of the chromatographic system was obtained from the optimization experiments for the purification of FLB. With this system. FLB has a capacity factor of 4.5 and is completely resolved from the impurities.

In previous experiments, the dissociation of the bound FLB fron the benzodiazepine receptors was examined by us. The highest recovery (90.8% of FLB) was achieved by dissociation with Tris-HCl buffer (pH 7.4; 50 mM), containing 10 µM flumazenil. To quantify the amount of dissociated FLB, 100 µl of the dissociation solution was injected directly into the HPLC-system. However, Tris-HCl buffer gave an enormous solvent peak, so that there was an insufficient resolution between the solvent peak and FLB. Acetate buffer (pH 4, 100 mM) also has the capability to dissociate the bound FLB from the receptors, with a recovery of 87.2%. Because acetate buffer did not cause such a solvent peak as Tris-HCl buffer, FLB could be quantified. FIG. 2 shows chromatograms of 10 nM solutions of FLB in Tris-HCl buffer and acetate buffer, respectively.

3.3 Binding Characteristics of FLB to the Benzodiazepire Receptor

Figure 4:
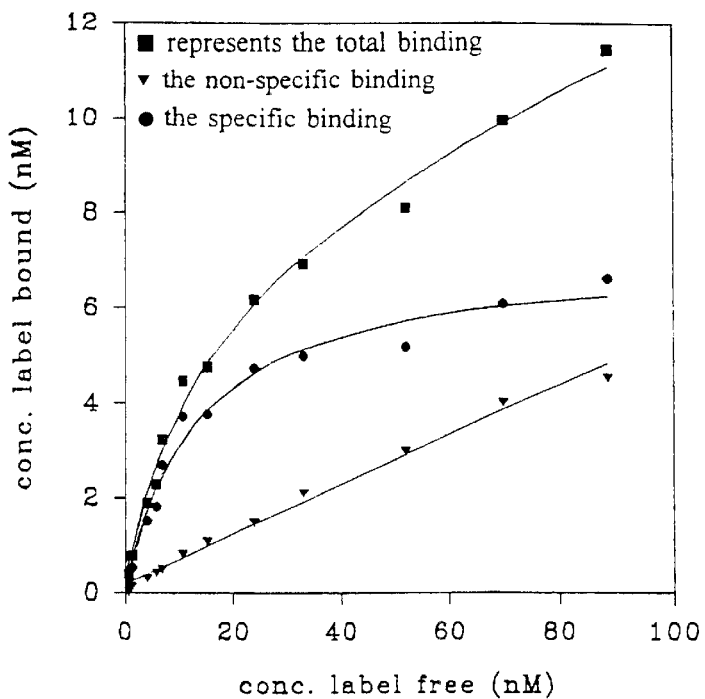
Figure 5:
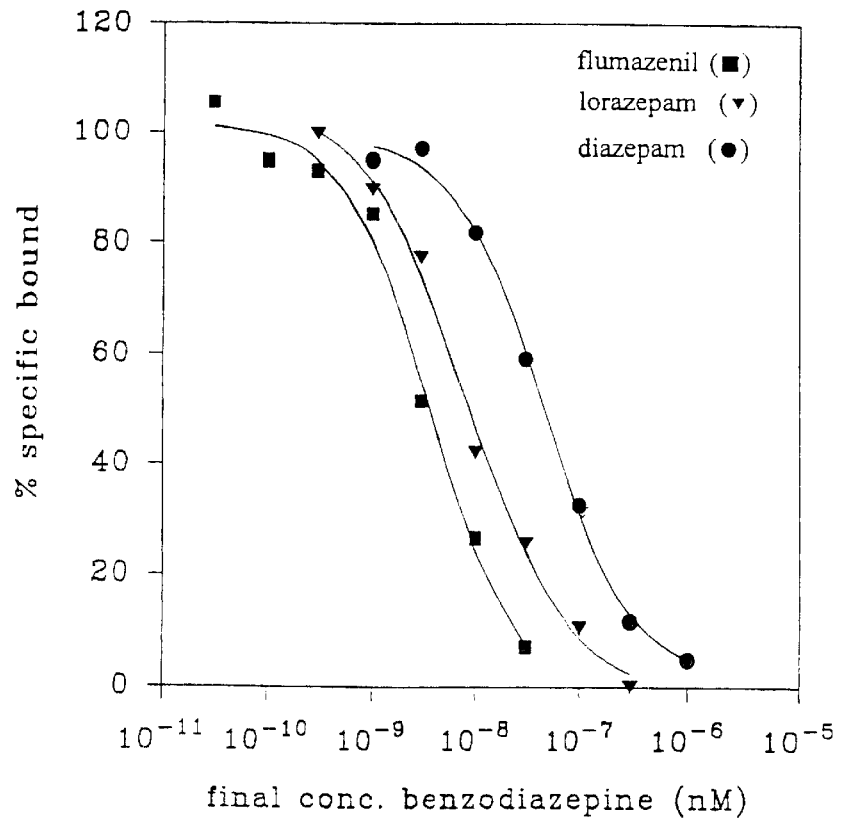

The saturation and inhibition curves for both the radioactive labeled benzodiazepine [$^3$H]flunitrazepam and the fluorescent labeled benzodiazepine. FLB, were fitted with the program ESDA-Ligand V4 (Biosoft, Cambridge. UK) using a one-binding site model. FIG. 4 shows a representative saturation curve of FLB. The specific binding was calculated by subtracting the non-specific binding from the total binding. The binding affinity of FLB for the benzodiazepine receptor was calculated to be 8.60=2.89 nM. This value is comparable with the affinity constant estimated with radioligand binding assays. Inhibition assays with [$^3$H] flunitrazepam gave a $K_i$-value of 6.5 nM For FLB. The $B_{max}$ value was calculated to be 3.42±0.01 nM, which corresponds to 3.84±0.09 pM/mg protein. In a previous study, we established a $B_{max}$ of 1.0 pM/mg protein [d]. As yet there is no explanation for this difference in $B_{max}$-values. This increase in binding sites cannot be assigned to extra binding sites for the fluorophore or the possibility that flumazenil has more binding sites than flunitrazepani, since FLB can be displaced completely by both diazepam, lorazepam and flumazenil (see FIG. 4). However, Havunjian et al. [g] also found a higher $B_{max}$ for the fluorescent-labeled benzodiazepine BD 623 (NBD-NH—$(CH_2)_3$-Ro15-3890, which is also a flumazenil derivative) than for [$^3$H]flumazenil, 7.2 versus 2.3 nM, respectively (their higher $B_{max}$-values can however be explained by the fact that they used receptor material from rat as opposed to our use of calf receptor material. As a possible explanation they brought up the difference in separation of bound and unbound fractions of labeled ligand between their two methods. Using [$^3$H] flumazenil, they used filtration, but with ED 623, they did not separate the bound and unbound fractions. After binding of BD 623 to the receptor, the fluorescence intensity is decreased and from the level of fluorescence quenching the amount of bound BD 623 can be estimated. However, they are uncertain whether the discrepancy can be explained by the difference in separation.

The non-specific binding of FLB was 25% of the total binding at a free initial concentration of 15 nM and was comparable with other fluorescent receptor assays for benzodiazepines. Takeuchi et al. [c] e.g. found in their time-resolved fluorometric assay with Eu-1012-S as labeled-benzodiazepine a non-specific binding of 27% and a non-specific binding of 20% in their fluorescent receptor assay with Ro7-1986-AMCA as labeled ligand [b].

3.4 Fluorescent Receptor Assay for Benzodiazeptnes

FLB was tested as fluorescent label by determining calibration curves of three benzodiazepines with different affinities for the benzodiazepine receptor, namely flumazenil, lorazepam and diazepam. These experiments were done with a FLB assay concentration of 7.3 nM. This concentration corresponds to the $K_d$ of FLB. Representative calibration curves are shown in FIG. 4.

With FLB as labeled ligand, the three benzodiazepines show the same order in affinity as when determined with a radioactive labeled ligand. The $IC_{50}$, values calculated from the calibration curves, are represented in Table 1.

TABLE 1

$IC_{50}$ values of different benzodiazepines.

| | $IC_{50}$ (nM) |
|---|---|
| flumazenil | 4.9 ± 1.5 |
| lorazepam | 7.2 ± 0.5 |
| diazepam | 41 ± 7 |

Figure 6:
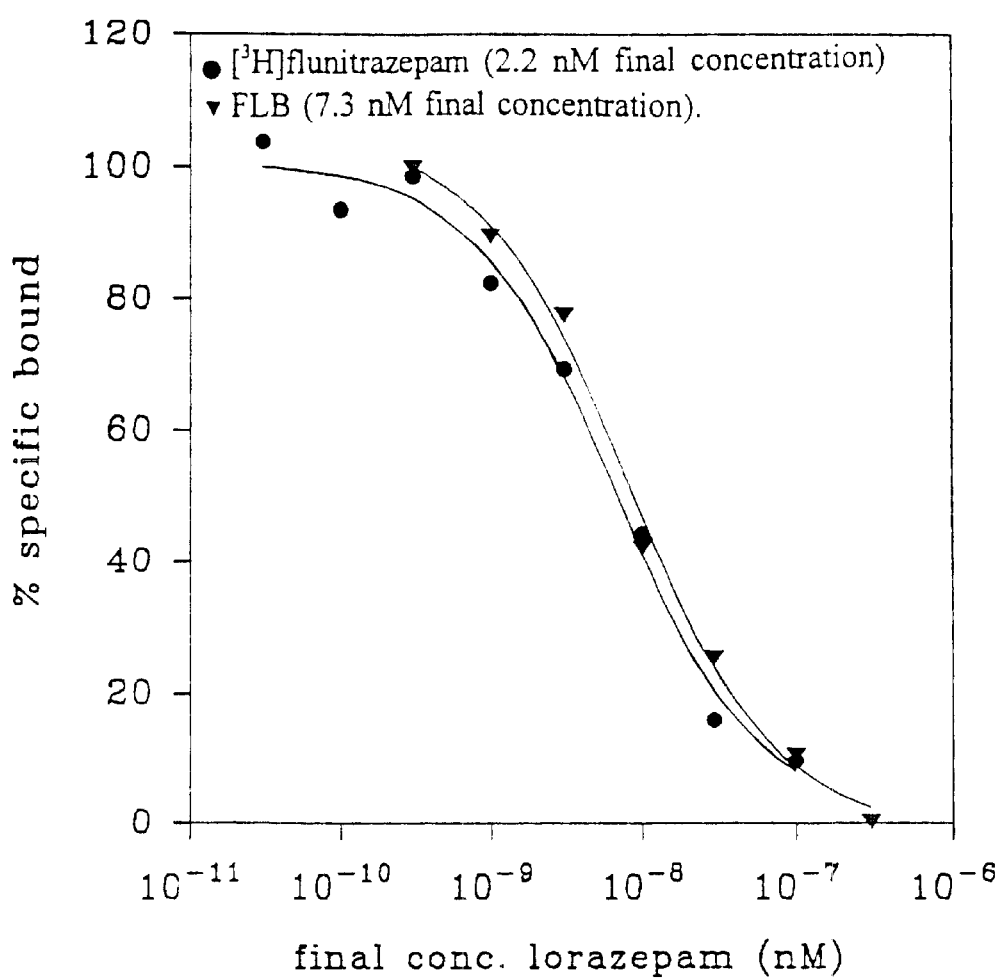

To compare the fluorescent receptor assay with radioreceptor assay, the calibration curves of lorazepam were determined with both the fluorescent label FLB and the radioactive label [$^3$H]flunitrazepam. As can be seen in FIG. 6, both curves are identical. The $IC_{50}$ of lorazepam, determined with [$^3$H]flunitrazepam as labeled ligand, was 6.61±0.69 nM and did not differ significantly from the $IC_{50}$, determined in the fluorescent receptor assay when compared to Student's t-test (p=0.451). This proves that receptor assays can be performed successfully with fluorescent labels. For comparing the $IC_{50}$-values of lorazepam, determined will two different ligands, instead of the $K_i$-values, the ratio between the concentration of free labeled ligand (L*) and $K_d$ of the labeled ligand has to be equal, since the connection between the $IC_{50}$ and the $K_i$ is expressed by the Cheng-Prusoff equation [k]:

$$IC_{50} = K_i * \left(1 - \frac{[L^*]}{K_d}\right)$$

In our experiments, this ratio is equal for both ligands, so the radio-receptor assay could be compared with the fluorescence receptor assay by comparing the $IC_{50}$-values.

By using a HPLC-system for the quantification of FLB, we avoided the interference of impurities of the receptor preparation. Besides, as in our assay the bound fractions rather than the unbound fractions are determined, the accuracy of the assay was markedly improved. In addition a receptor concentration of 2.8 mg/ml was used which provides an additional advantage over the methods of the state of the art. Ensing [1] e.g. had calculated that by increasing the receptor concentration, the detection limit can be decreased. Now an assay has been provided which offers low concentrations of receptor material whilst obtaining sensitive detection.

In conclusion the benzodiazepine receptor assay can be executed successfully with the fluorescent labeled benzodiazepine FLB. The time to perform a fluorescent receptor assay and to quantify the bound fractions is comparable with the time necessary for a radioreceptor assay. But the use of a fluorescent label in stead of a radioactive label has several advantages, such as the lower cost, less harmful for health etc. Besides, fluorescent receptor assays can also be executed in laboratory which are not equipped for work with radioactivity.

Acknowledgments

Mr. E. van Velsen from Millipore (Etten-Leur, The Netherlands) is thanked for supplying the MultiScreen Assay System.

References

[a] G. Wong, K. F. Koehler, P. Skolnick, Zi-Quang Gu, S. Ananthan, P. Schönholzer, W. Hunkeler, W. Zhang, J. M. Cook, J. Med. Chem. 1993. 36, p.1820–1830.

[b] T. Takeuchi and G. A. Rechnitz. Norisotopic receptor-binding assay for benzodiazepine receptors utilizing a fluorophore labeled ligand, Anal. Biochem. 194 (1991) 250–255.

[c] Takeuchi, T. Nishikawa, R. Matsukawa and J. Matsui. Nonisotopic receptor, assay for benzodiazepine drugs using time-resolved fluorometry, Anal. Chem. 67 (1995) 2655–2658.

[d] M. J. Janssen, M. Stegeman. K. Ensing and R. A. de Zeeuw. Solubilized benzodiazepine receptors for use in receptor assays, J. Pharm. Biomed. Anal., 14 (1996) 989–996.

[e] S. Ananthan, S. D. Clayton, S. E. Ealick, G. Wong, G. E. Evoniuk and P. Skolnick. Journal of Medicinal Chemistry. 1993, 36 p. 479–489.

[f] P. J. Munson and D. Rodbard, Ligand: A versatile computerized approach for characterization of ligand-binding systems, Anal. Biochem., 107 (1980) 220–239.

[g] R. H. Havunjian, B. R. de Costa, K. C. Rice and P.Skolnick, Characterization of benzodiazepine receptors with a fluorescence-quenching ligand, J. Biol. Chem., 265 (1990) 22181–22386.

[h] R. T. McCabe, B. R. de Costa, R. I. Miller, R. H. Havujian, K. C. Rice and P. Skolnick. Characterization of benzodiazepine receptors with fluorescent ligands, FASEB J., 4 (1990) 2934–2940.

[i] J. L. Velazquez. C. L. Thompson. E. M. Barnes and K. J. Angelides. Distribution and lateral mobility of GABA/benzodiazpine receptors on nerve cells, J. Neurosci., 9 (1989) 2163–2169.

[j] T. Takeuchi, M. Yoshida, Y. Kabasawa, R, Matsukawa. E. Tamiya and I. Karube. Time-resolved fluorescence receptor assay for benzodiazepines, Anal. Lett., 26 (1993) 1535–1545.

[k] Y.-C. Chen and W. H. Prusoff, Relationship between the inhibition constant ($K_i$) end the concentration of inhibition constant ($K_i$) and the concentration of inhibitor which causes 50 percent inhibition ($I_{50}$) of an enzymatic reaction. Biochem. Pharmacol., 22 (1973) 3099–3108.

[1] K Ensing. The radioreceptor assay, a tool for the bioanalysis of drugs, in: Bioanalysis of anticholinergics with muscarinic receptors in relation with chronic obstructive lung diseases. Ph.D, thesis, University of Groningen, 1984, pp 25–40.

What is claimed is:

1. A method for quantitatively and/or qualitatively assaying an analyte in a sample, with a non-radioactive assay, said analyte being a receptor binding compound, said method comprising the steps of
   a) contacting the sample with material comprising a receptor for said analyte in order for receptor-analyte binding to occur and
   b) further contacting the sample with a non-radioactive detectable ligand for the receptor in order for receptor-ligand binding to occur, followed by
   c) separating the resulting receptor bound and free fractions,
   d) subjecting the receptor bound fraction to dissociating conditions releasing the non-radioactive ligand from the receptor,
   e) assaying for the dissociated non-radioactive ligand so as to detect the detectable ligand, and
   f) determining presence or amount of said analyte from results of step (e);
   said receptor being present in a concentration between 0.5–5 nM,
   said non-radioactive detectable ligand being at least 90% pure,
   said non-radioactive detectable ligand being non radioactively detectable,
   said detectable ligand being added in an amount corresponding to the amount required for occupation by the ligand of 10–75% of the receptor material present in the assay in absence of analyte at a receptor concentration below the $K_d$ of the ligand and receptor under conditions otherwise corresponding to those of the assay, wherein $K_d$ is the equilibrium dissociation constant of the detectable ligand,
   said dissociating conditions and said non-radioactive detectable ligand being such that at least 90% bound ligand is released, in such a form that less than 10% of the resulting detectable product reassociates with the receptor,
   said dissociating conditions and said non-radioactive detectable ligand being selected such that the resulting dissociated ligand is quantitatively and/or qualitatively detectable, wherein when said method effects a quantitative assay of said analyte, said method further comprises determining analyte content in relation to calibration curves.

2. A method according to clam 1, wherein step a) and b) are carried out concomitantly.

3. A method according to claim 1, wherein step a) is carried out prior to step b).

4. A method according to claim 1 wherein the ligand and dissociation conditions are selected such that the ligand does not degrade under the dissociating conditions thereby yielding the detectable product.

5. A method according to claim 1, wherein the ligand and dissociation conditions are selected such that the ligand is completely and uniformly degraded thereby yielding the detestable product.

6. A method according to claim 1, wherein the amount of ligand added is equivalent to an amount within the range of 0.1–2.0*$K_d$ nM of the receptor and ligand.

7. A method according to claim 1, wherein the $K_d$ for the ligand and receptor is below 10 nM.

8. A method according to claim 1, wherein in step c) the bound fraction is separated on the basis of size difference from the free fraction.

9. A method according to claim 1, wherein the receptor material is derived from receptor containing tissue.

10. A method according to claim 1, wherein the receptor material is native receptor material obtained in vivo from an animal or microorganism.

11. A method according to claim 1, wherein the free fraction is separated in step c) from the bound fraction by filtration.

12. A method according to claim 1, wherein said contacting step is performed in a container comprising a filter, said filter being of such a nature to ensure the receptor material cannot pass the filter whereas the non bound ligand and analyte can, said step of separating the resulting receptor bound and free fractions is completed by filtering the resulting mixture and rinsing the filter, and wherein said step of subjecting the receptor bound fraction to dissociating conditions is completed by releasing the ligand from the receptor and passing the resulting solution though the filter into another vessel in order to detect the dissociated product for the detection of the detectable product.

13. A method according to claim 1, wherein the ligand is provided with a detectable label attached via a spacer.

14. A method according to claim 13 wherein the spacer comprises a carbon chain of between 2–10 carbon atoms.

15. A method according to claim 1, wherein the ligand is a flumazenil derivative.

16. A method according to claim 1, said dissociating conditions and said receptor material being such that no other compounds are released in an amount that can interfere with the detection of the released ligand.

17. A method according to claim 1, wherein the dissociating conditions comprise rinsing in conditions other than physiological conditions and under conditions which ensure the detectable ligand or detectable label of the ligand remain stable and functional i.e. conditions which in addition are not too aggressive.

18. A method according to claim 16, wherein the dissociating conditions exclude a pH between 6–8.

19. A method according to claim 17, wherein the conditions comprise a buffer with a pH between 3.5 and 4.5.

20. A method according to claim 1, wherein the detectable product provides a detectable signal in aqueous medium sufficient for quantification exhibiting a deviation of less than 10% from the real value.

21. A method according to claim 1, wherein the analyte is to be detected at a level below 1 micromolar.

22. A method according to claim 1, wherein the analyte is to be detected at a level of 1 picomolar or lower.

23. A method according to claim 1, wherein the receptor material is washed at least three times prior to contacting the sample with analyte.

24. A method as claimed in claim 1, wherein the analyte is to be determined in an aqueous system.

25. A method according to claim 1, wherein an additional separation step is carried out between the dissociation step and the detection step.

26. A method according to claim 25, wherein the fraction resulting from the dissociation step comprising free ligand is assayed using a HPLC chromatograph linked to a detector of the type required for detecting the detectable ligand.

27. A method according to claim 25, wherein the fraction resulting from the dissociation step comprising free ligand is assayed using GLC linked to a detector of the type required for detecting the detectable ligand.

28. A method according to claim 1, wherein the detectable ligand can be determined via a technique selected from the group consisting of FID (flame ionisation detection), ECD (electron capture detection), NPD (nitrogen phosphor detection) and mass spectrometry.

29. A method according to claim 1, wherein the detectable ligand can be determined via a technique selected from the group consisting of fluorescence, chemoluminescence, luminescence, mass spectrometry and electrochemical detection.

30. A method according to claim 1, wherein the detectable product is detectable with fluorescence technology.

31. A method according to claim 1, wherein the ligand is provided with a fluorescent label.

32. A method according to claim 1, wherein the ligand is the fluorescent ligand FLB (fluorescent-labeled benzodiazepine).

33. A method according to claim 1, wherein the ligand provides a fluorescent signal in aqueous medium with at least the strength of 0.2*the signal of 1M quinine standard in 1M $H_2SO_4$.

34. A method according to claim 1, wherein the receptor material is membrane bound receptor material.

35. A method according to claim 1, wherein the receptor material is a membrane receptor selected from the group consisting of adenosine, adrenergic, dopamine, histamine, muscarinic, acetylcholinergic, nicotinic, opiate, serotin, benzodiazepine, GABA (gamma amino butyrate), glycine, calcium channel, sodium channel, chemotactic peptide, EFG (epidermal growth factor), glucocorticoid, cannabinoid, cholecystokinin, cytokines, leukotriene and neurokinin receptors.

36. A method according to claim 1, wherein the receptor material is obtained from a pellet derived by centrifugation of a supernatant comprising said receptor material.

37. A method according to claim 1, wherein the amount of receptor material when the separation step uses a filter is lower than the amount of receptor that will clog the filter.

38. A method according to claim 1, wherein the amount of receptor material when the separation step uses a filter is lower than the amount of receptor that will clog the filter, and wherein the amount of receptor is less than 1–4 mg/ml lyophilised receptor material per 0.2 $cm^2$ of filter area.

39. A method according to claim 1, wherein the amount of receptor material is equivalent to that present in P2 pellet derived from receptor containing tissue, said P2 pellet having a concentration equal to 0.5–5 pmol/mg protein.

40. A method according to claim 1, wherein the receptor material is a benzodiazepine sensitive receptor.

41. A method according to claim 1, wherein the receptor material is soluble or solubilized receptor material.

42. A method according to claim 41 wherein the soluble receptor material is a receptor of a steroid hormone selected from the group consisting of androgen, estrogen and progesterone.

43. A method according to claim 41, wherein the receptor is an oestrogen receptor.

44. A method according to claim 43, wherein the detectable ligand is coumestrol.

45. A method according to claim 41, wherein the soluble or solubilized receptor material has been subjected to treatment enabling separation via filtration in step c) such that the receptor bound fraction cannot pass the filter upon filtration.

46. A method according to claim 45, wherein the treatment comprises precipitation with protamines.

47. A method according to claim 41, wherein the soluble receptor material is a membrane receptor selected from the group consisting of adenosine, adrenergic, dopamine, histamine, muscarinic (or acetylcholinergic), nicotinic, opiate, serotin, benzodiazepine, GABA, glycine, calcium channel, sodium channel, chemotactic peptide, EGF (epidermal growth factor), glucocorticoid, cannabinoid, cholecystokinin, cytokines, leukotriene and neurokiniin receptors.

48. A method according to claim 1, wherein said detectable ligand is attached to a fluorophore via a spacer, wherein said spacer comprises a terminal carboxy group.

49. A method for quantitatively and/or qualitatively assaying an analyte in a sample, with a non-radioactive assay, said analyte being a receptor binding compound, said method comprising the steps of a) contacting the sample with material comprising a receptor for said analyte in order for receptor-analyte binding to occur and b) further contacting the sample with a non-radioactive detectable ligand for the receptor in order for receptor-ligand binding to occur, followed by c) separating the resulting receptor bound and free fractions, d) subjecting the receptor bound fraction to dissociating conditions releasing the non-radioactive ligand from the receptor, e) assaying for the dissociated ligand so as to detect the detectable ligand, and f) determining presence or amount of said analyte from results of step (e);

said receptor being present in a concentration between 0.5–5 nM, said non-radioactive detectable ligand being at least 90% pure, said non-radioactive detectable ligand being non radioactively detectable, said non-radioactive detectable ligand being added in an amount corresponding to the amount required for occupation by the ligand of 10–75% of the receptor material present in the assay in absence of analyte at a receptor concentration below the $K_d$ of the ligand and receptor under conditions otherwise corresponding to those of the assay, wherein $K_d$ is the equilibrium dissociation constant of the detectable ligand, said dissociating conditions and said non-radioacitve detectable ligand being such that at least 90% bound ligand is released, in such a form that less than 10% of the resulting detectable product reassociates with the receptor, said dissociating conditions and said non-radioactive detectable ligand being selected such that the resulting dissociated ligand is quantitatively and/or qualitatively detectable;

wherein said non-radioactive detectable ligand is attached to a fluorophore via a spacer, wherein when said method effects a quantitative assay of said analyte, said method further comprises determining analyte content in relation to calibration curves.

* * * * *